United States Patent
Brooke et al.

(10) Patent No.: US 7,761,157 B2
(45) Date of Patent: *Jul. 20, 2010

(54) CARDIAC STIMULATION AND SENSING WITH ENDOLYMPHATICALLY IMPLANTED LEAD

(75) Inventors: M. Jason Brooke, Minneapolis, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 501 days.

This patent is subject to a terminal disclaimer.

(21) Appl. No.: 11/675,696

(22) Filed: Feb. 16, 2007

(65) Prior Publication Data

US 2007/0282380 A1 Dec. 6, 2007

Related U.S. Application Data

(63) Continuation-in-part of application No. 11/422,423, filed on Jun. 6, 2006.

(51) Int. Cl.
*A61N 1/365* (2006.01)

(52) U.S. Cl. .................. 607/17; 607/6; 607/18; 607/22; 600/300; 600/301; 600/515

(58) Field of Classification Search ........ 607/2, 607/4, 5, 9, 32, 37, 115, 116, 6, 18, 22; 600/509, 600/300, 301
See application file for complete search history.

(56) References Cited

U.S. PATENT DOCUMENTS

| | | |
|---|---|---|
| 3,814,080 A | 6/1974 | Norman |
| 3,916,875 A | 11/1975 | Toch |
| 4,792,330 A | 12/1988 | Lazarus et al. |
| 4,957,484 A | 9/1990 | Murtfeldt |
| 5,135,004 A | 8/1992 | Adams et al. |
| 5,391,143 A | 2/1995 | Kensey |
| 5,531,768 A | 7/1996 | Alferness |
| 5,655,548 A | 8/1997 | Nelson et al. |
| 5,865,744 A | 2/1999 | Lemelson |
| 6,108,577 A | 8/2000 | Benser |
| 6,272,370 B1 | 8/2001 | Gillies et al. |

(Continued)

FOREIGN PATENT DOCUMENTS

WO WO-2004/006795 A1 1/2004

(Continued)

OTHER PUBLICATIONS

Gray, Henry."Anatomy of the Human Body". Philadelphia: Lea & Febiger, 1918; Bartleby.com, 2000. www.bartleby.com/107/, 3 pages.*

(Continued)

*Primary Examiner*—Carl H Layno
*Assistant Examiner*—Gary A Porter, Jr.
(74) *Attorney, Agent, or Firm*—Faegre & Benson LLP

(57) ABSTRACT

A technique utilizing an endolymphatically implanted lead having one or more electrodes that may be used for sensing cardiac activity and/or delivering cardiac electrical stimulation by an implantable cardiac device. An electrode disposed in the thoracic duct is in close proximity to the left ventricle and generates an electrogram especially suitable for ischemia detection and/or discriminating between ventricular tachycardias and supraventricular tachycardias.

10 Claims, 3 Drawing Sheets

U.S. PATENT DOCUMENTS

| | | |
|---|---|---|
| 6,321,109 B2 | 11/2001 | Ben-Haim et al. |
| 6,368,284 B1 | 4/2002 | Bardy |
| 6,370,417 B1 | 4/2002 | Horbaschek et al. |
| 6,475,223 B1 | 11/2002 | Werp et al. |
| 6,741,882 B2 | 5/2004 | Schaffter et al. |
| 6,827,690 B2 | 12/2004 | Bardy |
| 6,913,577 B2 | 7/2005 | Bardy |
| 7,072,711 B2 | 7/2006 | Girouard et al. |
| 7,299,087 B2 | 11/2007 | Bardy |
| 7,317,941 B2 * | 1/2008 | Stomberg et al. ........... 600/509 |
| 7,437,191 B2 | 10/2008 | Pastore et al. |
| 7,460,906 B2 | 12/2008 | Libbus |
| 7,486,991 B2 | 2/2009 | Libbus et al. |
| 2001/0041870 A1 | 11/2001 | Gillis et al. |
| 2002/0029037 A1 | 3/2002 | Kim |
| 2002/0123674 A1 | 9/2002 | Plicchi et al. |
| 2002/0188253 A1 | 12/2002 | Gordon et al. |
| 2003/0105506 A1 | 6/2003 | Krishnan et al. |
| 2003/0113303 A1 | 6/2003 | Schwartz |
| 2003/0204185 A1 | 10/2003 | Sherman et al. |
| 2004/0015193 A1 * | 1/2004 | Lamson et al. ................. 607/9 |
| 2004/0102804 A1 | 5/2004 | Chin |
| 2004/0106953 A1 | 6/2004 | Yomtov et al. |
| 2004/0210118 A1 | 10/2004 | Letort |
| 2005/0043675 A1 | 2/2005 | Pastore et al. |
| 2005/0043765 A1 * | 2/2005 | Williams et al. ............... 607/9 |
| 2005/0080346 A1 | 4/2005 | Gianchandani et al. |
| 2005/0143765 A1 | 6/2005 | Bachmann et al. |
| 2005/0143779 A1 | 6/2005 | Libbus |
| 2005/0149014 A1 | 7/2005 | Hauck et al. |
| 2005/0149129 A1 | 7/2005 | Libbus et al. |
| 2005/0228471 A1 * | 10/2005 | Williams et al. ............ 607/126 |
| 2006/0020333 A1 | 1/2006 | Lashinski et al. |
| 2006/0206158 A1 | 9/2006 | Wu et al. |
| 2006/0217779 A1 * | 9/2006 | Ransbury et al. ............... 607/36 |
| 2006/0247686 A1 | 11/2006 | Girouard et al. |
| 2007/0021731 A1 | 1/2007 | Garibaldi et al. |
| 2007/0027460 A1 | 2/2007 | Case et al. |
| 2008/0009719 A1 | 1/2008 | Shuros et al. |
| 2008/0058661 A1 | 3/2008 | Bardy |
| 2008/0058881 A1 | 3/2008 | Wagner et al. |
| 2008/0086185 A1 | 4/2008 | Amurthur et al. |
| 2008/0132972 A1 | 6/2008 | Shuros et al. |
| 2009/0048641 A1 | 2/2009 | Libbus |

FOREIGN PATENT DOCUMENTS

| | | |
|---|---|---|
| WO | WO-2004006795 A1 | 1/2004 |
| WO | WO-2007/146493 A1 | 12/2007 |

OTHER PUBLICATIONS

"U.S. Appl. No. 11/422,423, Response filed Feb. 9, 2009 to Non-Final Office Action mailed Oct. 8, 2008", 8 pgs.

"U.S. Appl. No. 11/422,423, Non-Final Office Action mailed Jan. 10, 2008", 10 pgs.

"U.S. Appl. No. 11/422,423, Non-Final Office Action mailed Oct. 8, 2008", 9 pgs.

"U.S. Appl. No. 11/422,423, Response filed May 12, 2008 to Non-Final Office Action mailed Jan. 10, 2008", 12 pgs.

"U.S. Appl. No. 11/422,423, Non-Final Office Action mailed Jun. 1, 2009", 7 pgs.

"International Application Serial No. PCT/US2007/06178, International Search Report mailed Oct. 31, 2007", 5 pgs.

"International Application Serial No. PCT/US2007/06178, Written Opinion mailed Oct. 31, 2007", 8 pgs.

Pulley, M. S., et al., "Intravenous, intralesional and endolymphatic administration of lymphokines in human cancer.", *Lymphokine Research.*, vol. 5, Supplement 1, (1986), S157-S163.

Shuros, A. C., "Amelioration of Chronic Pain by Endolymphatic Stimulation", U.S. Patent Appl. No. 11/422,414, filed Jun. 6, 2006, 15 pgs.

Shuros, A. C., "Method and Apparatus for Gastrointestinal Stimulation Via the Lymphatic System", U.S. Appl. No. 11/422,418, filed Jun. 6, 2006, 35 pgs.

Shuros, A. C, et al., "Method and Apparatus for Neural Stimulation Via the Lymphatic System", U.S. Appl. No. 11/422,421, filed Jun. 6, 2006, 35 pgs.

Shuros, A. C, et al., "Method and Device for Lymphatic System Monitoring", U.S. Appl. No. 11/422,417, filed Jun. 6, 2006, 15 pgs.

"U.S. Appl. No. 11/422,423 , Non-Final Office Action mailed Nov. 30, 2009.", 11 Pgs.

"U.S. Appl. No. 11/422,423, Response filed Sep. 1, 2009 to Non Final Office Action mailed Jun. 1, 2009", 8 pgs.

"European Application Serial No. 07782375.5 office action mailed Aug. 10, 2009", 4 pgs.

* cited by examiner

CARDIAC STIMULATION AND SENSING WITH ENDOLYMPHATICALLY IMPLANTED LEAD

RELATED APPLICATIONS

This application is a continuation-in-part of co-pending U.S. patent application Ser. No. 11/422,423, filed on Jun. 6, 2006, which is hereby incorporated by reference.

FIELD OF THE INVENTION

This invention pertains to cardiac rhythm management devices such as pacemakers and implantable cardioverter/defibrillators.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Pacing therapy may also be used in treatment of cardiac conduction disorders in order to improve the coordination of cardiac contractions, termed cardiac resynchronization therapy. Other cardiac rhythm management devices are designed to detect atrial and/or ventricular tachyarrhythmias and deliver electrical stimulation in order to terminate the tachyarrhythmia in the form of a cardioversion/defibrillation shock or anti-tachycardia pacing. Certain combination devices may incorporate all of the above functionalities. Any device with a pacing functionality will be referred to herein simply as a pacemaker regardless of other functions it may be capable of performing.

Cardiac rhythm management devices such as described above monitor the electrical activity of heart via one or more sensing channels so that pacing pulses or defibrillation shocks can be delivered appropriately. Such sensing channels include implanted leads which have electrodes disposed internally near the heart, which electrodes may also be used for delivering pacing pulses or defibrillation shocks through pacing or shock channels. The signals generated from the sensing channels are intra-cardiac electrograms and reflect the time course of depolarization and repolarization as the heart beats, similar to a surface electrocardiogram (ECG). Implantable devices may also incorporate one or more subcutaneously disposed electrodes (e.g., on the surface of the device housing) into a sensing channel for generating an electrogram signal, referred to herein as a subcutaneous ECG. A subcutaneous ECG is more similar in its morphology characteristics to a surface ECG than is an intra-cardiac electrogram. The electrogram signals generated from the sensing channels of an implanted device, whether an intra-cardiac electrogram or a subcutaneous ECG, may be transmitted wirelessly to an external device where they can be displayed and analyzed in much the same manner as a surface electrocardiogram.

SUMMARY

Described herein is a technique utilizing an endolymphatically implanted lead having one or more electrodes that may be used for sensing cardiac activity and/or delivering cardiac electrical stimulation by an implantable cardiac device. An electrode disposed in the thoracic duct is in close proximity to the left ventricle and generates an electrogram especially suitable for ischemia detection and/or discriminating between ventricular tachycardias and supraventricular tachycardias. Such an endolymphatic electrogram may also exhibit morphology characteristics similar to a subcutaneous ECG. A shocking vector produced with a shock electrode in the thoracic duct may be configured to pass directly through the left ventricular muscle mass. A defibrillation shock delivered with such a vector may therefore exhibit a lowered defibrillation threshold and allow for lower shock energies. Sensing and/or stimulation channels may be configured with an endolymphatically implanted electrode together with one or more additional electrodes such as the implantable device housing, a subcutaneous electrode, or an intra-cardiac electrode.

DETAILED DESCRIPTION

Current implantable cardiac devices typically utilize shock electrode implantation within the right ventricle, superior vena cava, subcutaneously and/or submuscularly. Various vectors and protocols are used to defibrillate the heart. As a result of the electrode locations, defibrillation typically results in excessive skeletal muscle contraction and significant pain. Furthermore, existing shock vectors can result in unnecessarily high defibrillation thresholds (DFT). Described herein is a method and device in which one or more electrodes and/or leads are implanted in a lymphatic vessel (e.g. thoracic duct) for the use of delivering an electrical stimulation (i.e. a defibrillation shock or low-voltage pace) to the heart. The proximity of the thoracic duct to the heart provides an excellent means by which defibrillation and pacing of the heart could be produced. This is due to the fact that the stimulation vector travels across the largest myocardial mass of the heart, the left ventricle. Adding an electrode in the thoracic duct provides an additional vector by which the shock or pace can be delivered (e.g. as a cathode or anode). In addition, shock protocols can incorporate this additional shocking electrode as a first option or alternative to existing protocols, while pacing programming can incorporate this additional electrode as a first or alternative pacing vector (i.e. electronic repositioning). Furthermore, an endolymphatically implanted stimulation electrode may eliminate the need for shock/pace electrodes beyond the thoracic cavity (i.e. subcutaneous or submuscular electrodes), and minimize the skeletal muscle contraction and pain specifically associated with defibrillation shocks. The location of the electrode within the thoracic duct could also reduce the DFT. An endolymphatically implanted electrode can be incorporated into any defibrillation and/or pacing system (i.e., a pacemaker, implantable cardioverter defibrillator, cardiac resynchronization therapy pacemaker, cardiac resynchronization therapy defibrillator, subcutaneous ICD, etc.). An endolymphatically implanted electrode also provides an additional sensing vector that generates an electrogram especially suitable for morphology analysis in order to detect cardiac ischemia. The sensing vector may be configured to pass directly across the left ventricular mass (e.g., with a sensing vector from a right ventricular electrode to a thoracic duct electrode), making ischemia detection in the left ventricle more accurate. An endolymphatic sensing vector may also be advantageously used for cardiac arrhythmia detection such as discrimination between ventricular tachycardias and supraventricular tachycardias.

1. Exemplary Implantable Device Description

Figure 1:
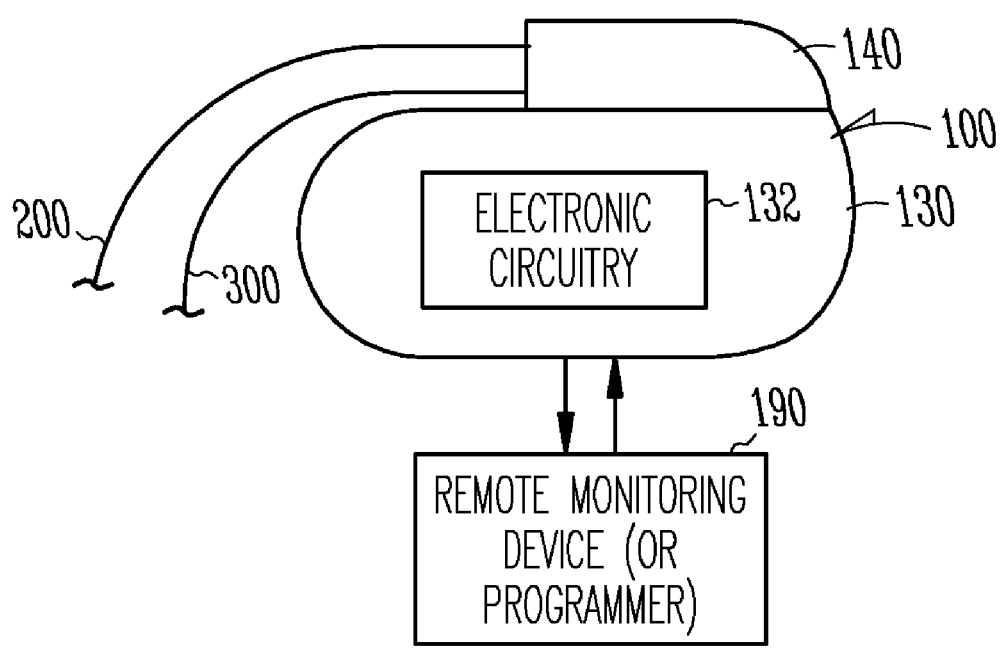
FIG. 1 shows the external components of an implantable cardiac device.

Cardiac rhythm management devices are implantable devices that provide electrical stimulation to selected chambers of the heart in order to treat disorders of cardiac rhythm. Such devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site. FIG. 1 shows the components of an implantable device 100 that includes a hermetically sealed housing 130 that may be implanted placed subcutaneously or submuscularly in a patient's chest. The housing 130 may be formed from a conductive metal, such as titanium, and may serve as an electrode for delivering electrical stimulation or sensing in unipolar or multipolar configurations. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. The external programmer or monitoring device 190 may also be configured to analyze data received from the implantable device. The leads 200 and 300 each have one or more electrodes incorporated therein that are typically disposed in an intra-cardiac location (i.e., in the right atrium or ventricle or in the coronary sinus) for stimulation and/or sensing of the heart.

Figure 2:
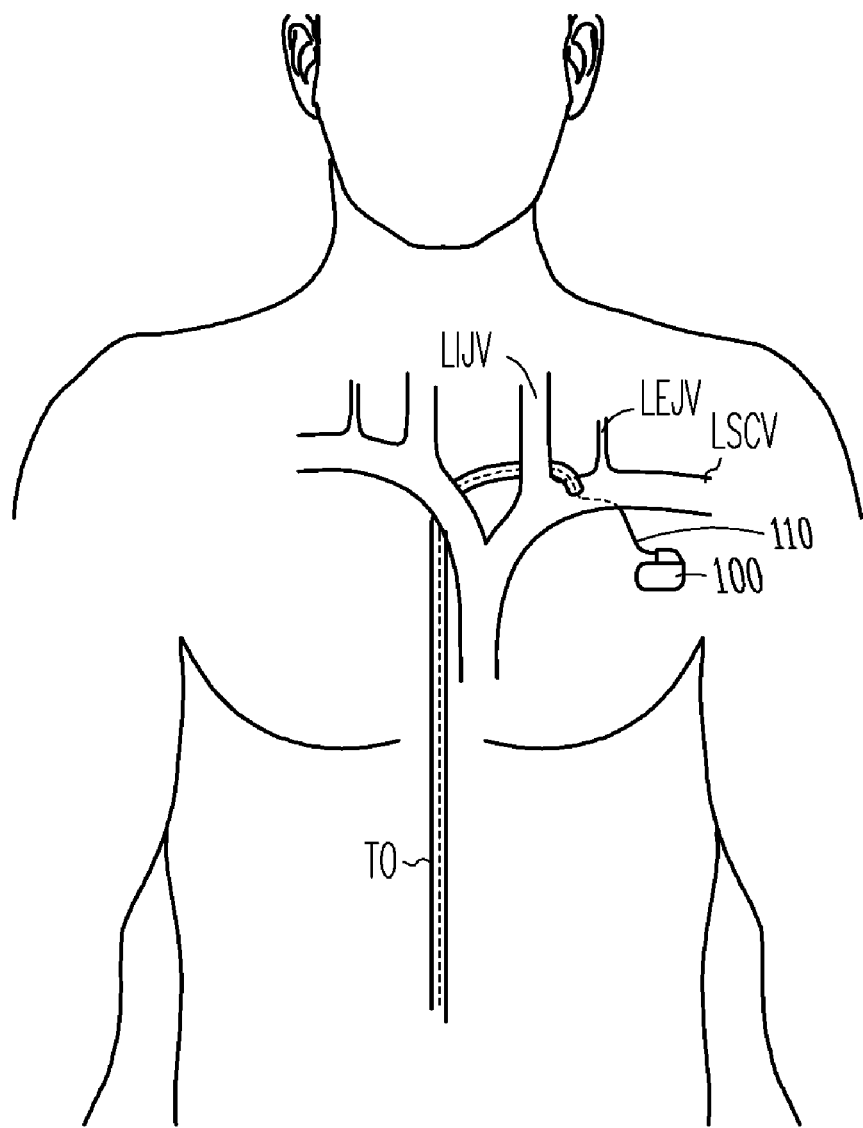
FIG. 2 illustrates the physical placement of an implantable cardiac device with an endolymphatic electrode.

FIG. 2 shows an implantable cardiac device 100 with a lead 110 incorporating one or more electrodes that are advantageously implanted in the thoracic duct TD rather than an intra-cardiac location. Such an endolymphatically implanted electrode may be incorporated into a sensing channel for generating electrograms that can be used for detection of chamber senses signifying contraction or for morphological analysis. An endolymphatically implanted electrode may also be used to stimulate the heart by incorporating the electrode into a stimulation channel such as a pacing or shock channel. The sensing or stimulation channels incorporating a endolymphatically implanted electrode may also incorporate other electrodes such as intra-cardiac electrodes disposed in an atrium or ventricle, epicardial electrodes disposed on the heart surface, and/or the device housing to form different sensing and/or stimulation vectors. FIG. 2 also illustrates relevant portions of the lymphatic and venous system including portions of the thoracic duct TD, left subclavian vein LSCV, left external jugular vein LEJV, and left internal jugular vein LIJV. The thoracic duct connects to the left subclavian vein at the juncture of subclavian vein and the left internal jugular vein. Lymphatic fluid from the lower body flows up the thoracic duct and empties into the left subclavian vein. FIG. 2 shows that the lead 110 from the implantable device is introduced into the venous system via the subclavian vein and from there into the thoracic duct. Specific techniques for implanting a lymphatic instrument such as an endolymphatic electrode are described in U.S. application Ser. No. 11/422,423, filed on Jun. 6, 2006, incorporated by reference.

Figure 3:
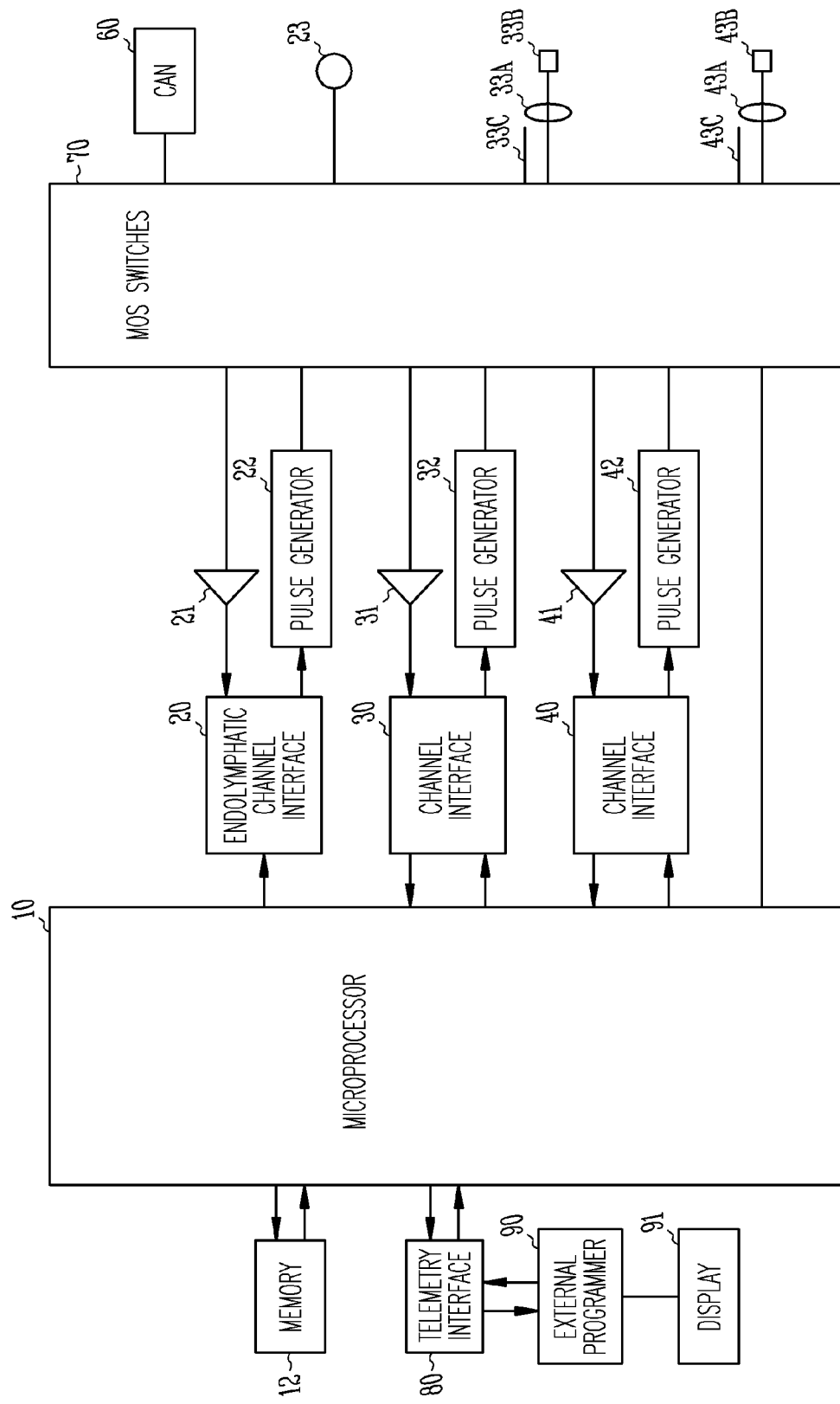
FIG. 3 is a block diagram of an exemplary cardiac rhythm management device having an endolymphatic sensing/stimulation channel.

A system diagram of an implantable cardiac rhythm management device is shown in FIG. 3. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external programmer 90 or other device via a wireless telemetry link. The external programmer 90 is a computerized device which can be used to program the implantable device and receive data from it. A display 91 or other output means allows the external programmer to display received data, such as recorded or near real-time electrograms.

The device may configure its available electrodes into either stimulation or sensing channels. A stimulation channel may be either a pacing channel or a shock channel depending upon the type of electrical pulse delivered through the channel and is made up of a pulse generator connected to an electrode. A sensing channel is made up of the sense amplifier connected to an electrode. The MOS switch matrix 70 controlled by the microprocessor is used to switch the electrodes from the input of a sense amplifier to the output of a pulse generator. The switch matrix 70 also allows the sensing and stimulation channels to be configured by the controller with different combinations of the available electrodes in either unipolar, bipolar, or multipolar configurations. In a bipolar configuration, two closely spaced electrodes usually on the same lead form the sensing or stimulation channel. In a unipolar configuration, the sensing or stimulation channel is formed by an electrode referenced to the conductive housing or other distantly disposed electrode. A multipolar configuration incorporates three or more electrodes to form a sensing or stimulation vector between the electrodes. In an example configuration, one sensing/pacing channel includes ring electrode 43a and tip electrode 43b of bipolar lead 43c, sense amplifier 41, pulse generator 42, and a channel interface 40 while another sensing/pacing channel includes ring electrode 33a and tip electrode 33b of bipolar lead 33c, sense amplifier 31, pulse generator 32, and a channel interface 30. The channels may be configured, for example, as either atrial or ventricular channels depending upon the location of the electrode incorporated into the channel. A dedicated endolymphatic sensing or stimulation channel is also shown made up of a channel interface 20, sense amplifier 21, pulse generator 22, and an electrode 23 which can be disposed in the thoracic duct. The endolymphatic electrode 23 may be, for example, a ring-tip type of electrode or a coil electrode, the latter being more suitable for delivering shocks and for generating electrograms reflective of global cardiac activity. More than one endolymphatic electrode may be provided, and the switch matrix may configure the sensing or stimulation vector of the endolymphatic channel by referencing the electrode 23 to the device housing or can 60 and/or to intra-cardiac electrodes. The channel interfaces communicate bi-directionally with microprocessor 10 and may include analog-to-digital converters for digitizing sensing signal inputs from the sensing amplifiers, registers that can be written to for adjusting the gain and threshold values of the sensing amplifiers, and registers for controlling the output of pacing or shock pulses and/or changing the pulse amplitude.

The controller controls the overall operation of the device in accordance with programmed instructions stored in memory and with information derived from the sensing channels. The voltages sensed by the sensing electrodes are electrogram signals that are analogous to a surface ECG and provide a temporal record of cardiac depolarization and repolarization that occurs during either intrinsic or paced beats. The sensing circuitry of the pacemaker generates atrial and ventricular senses when voltages sensed by the electrodes of a particular channel exceed a specified threshold. A ventricular sense would correspond to an R wave on an ECG, and an atrial sense would correspond to a P wave. The controller interprets sense signals from the sensing channels in order to detect arrhythmias and to control the delivery of paces in accordance with a pacing algorithm that employs such senses to trigger or inhibit pacing. The electrogram signals can also be digitized and recorded (i.e., stored in memory) by the controller and then either transmitted via a telemetry link 80 to an external programmer or maintained in memory or other storage medium for later transmission. The patient's cardiac activity may thus be observed in real-time or over a selected historical period.

2. Endolymphatic Electrograms

An electrogram signal recorded from an endolymphatic channel having a thoracic duct electrode referenced to the implantable device housing has a sensing vector that passes directly through the left ventricle. Such an endolymphatic electrogram is thus more reflective of the depolarization pattern of the left ventricle than is an intra-cardiac electrogram. An endolymphatic electrogram is especially suitable for morphology analysis in order to detect, for example, particular cardiac arrhythmias or cardiac ischemia and may also be used instead of a subcutaneous ECG to approximate a surface ECG for morphology analysis. Such morphology analyses may be performed by the implantable device controller or by an external programmer or other device that receives the endolymphatic electrogram.

The implantable or external device may be configured to detect cardiac ischemia from a morphology analysis of an endolymphatic electrogram collected during an intrinsic or a paced beat, the latter sometimes referred to as an evoked response. When the blood supply to a region of the myocardium is compromised, the supply of oxygen and other nutrients can become inadequate for enabling the metabolic processes of the cardiac muscle cells to maintain their normal polarized state. An ischemic region of the heart therefore becomes abnormally depolarized during at least part of the cardiac cycle and causes a current to flow between the ischemic region and the normally polarized regions of the heart, referred to as a current of injury. A current of injury results in an abnormal change in the electrical potentials measured by an electrogram. If the abnormal depolarization in the ventricles lasts for the entire cardiac cycle, a zero potential is measured only when the rest of the ventricular myocardium has depolarized, which corresponds to the time between the end of the QRS complex and the T wave in an electrogram and is referred to as the ST segment. After repolarization of the ventricles, marked by the T wave in an electrogram, the measured potential is influenced by the current of injury and becomes shifted, either positively or negatively depending upon the location of the ischemic region, relative to the ST segment. Traditionally, however, it is the ST segment that is regarded as shifted when an abnormal current of injury is detected by an electrogram or electrocardiogram. A current injury produced by an ischemic region that does not last for the entire cardiac cycle may only shift part of the ST segment, resulting in an abnormal slope of the segment. A current of injury may also be produced when ischemia causes a prolonged depolarization in a ventricular region which results in an abnormal T wave as the direction of the wave of repolarization is altered.

In order for the device to detect a change in an endolymphatic electrogram indicative of ischemia, a recorded endolymphatic electrogram is analyzed and compared with a reference electrogram that serves as a template. Such a reference electrogram is preferably recorded with a similar sensing vector to ensure similar morphologies, referred to as an endolymphatic reference electrogram. The endolymphatic reference electrogram may either be a complete recorded endolymphatic electrogram or particular reference values representative of an endolymphatic electrogram. One way to look for an increased current of injury in the recorded endolymphatic electrogram is to compare the ST segment amplitude and/or slope with the amplitude and slope of the reference endolymphatic electrogram. Various digital signal processing techniques may be employed for the analysis, such as using first and second derivatives to identify the start and end of an ST segment. Other ways of looking for a current injury may involve, for example, cross-correlating the recorded and reference endolymphatic electrograms to ascertain their degree of similarity. The endolymphatic electrogram could be implicitly recorded in that case by passing the electrogram signal through a matched filter that cross-correlates the signal with the reference endolymphatic electrogram. The ST segment of the endolymphatic electrogram could also be integrated, with the result of the integration compared with a reference value derived from a reference endolymphatic electrogram to determine if an increased current of injury is present.

The implantable or external device may also be configured to perform a morphology analysis on an endolymphatic electrogram in order to detect or discriminate between cardiac arrhythmias. Arrhythmia detection may be performed by comparing a recorded endolymphatic electrogram with a reference endolymphatic electrogram, which may be either an entire electrogram or features derived therefrom, in order to detect specific changes in the recorded endolymphatic electrogram indicative of a particular arrhythmia. For example, ventricular tachycardia (VT) is an arrhythmia arising from abnormal spontaneous activity in the ventricles while a supraventricular tachycardia (SVT) arises from abnormal atrial activity. Morphology analysis of an endolymphatic electrogram may be used as one criteria for discriminating between VT and SVT so that an appropriate therapy may be delivered.

3. Endolymphatic Shock Channel

Cardioversion (an electrical shock delivered to the heart synchronously with an intrinsic depolarization) and defibrillation (an electrical shock delivered without such synchronization) can be used to terminate most tachycardias, including SVT, VT, and ventricular fibrillation (VF). As used herein, the term defibrillation should be taken to mean an electrical shock delivered either synchronously or not in order to terminate a fibrillation. In electrical defibrillation, a current depolarizes a critical mass of myocardial cells so that the remaining myocardial cells are not sufficient to sustain the fibrillation. The electric shock may thus terminate the tachyarrhythmia by depolarizing excitable myocardium, which prolongs refractoriness, interrupts reentrant circuits, and discharges excitatory foci.

Typically, shock electrodes are electrically conductive coils. The electric field vector applied to the heart when a shock is delivered is determined by the magnitude of the voltage pulse and the physical arrangement of the shocking electrodes, which may serve to concentrate the field in a particular region of the heart. Thus, the particular electrode arrangement used will dictate how much depolarizing current is necessary in order to terminate a given tachyarrhythmia. The defibrillation threshold (DFT) is the smallest amount of energy that can be delivered to the heart to reliably revert the fibrillation to normal sinus rhythm. Electrical energy delivered to the heart has the potential to both cause myocardial injury and subject the patient to pain. Whether or not a particular patient is a suitable candidate for ICD implantation is determined in part by that patient's defibrillation threshold, since too high a threshold would necessitate electrical shock therapy at levels that are dangerous for the patient. Furthermore, the larger the magnitude of the shocks delivered by an ICD, the more the battery is drained, thus decreasing the longevity of the device. It is desirable, therefore, for the defibrillation threshold to be as small as possible in order to minimize the amount of shocking current that the device must deliver in order to terminate a given tachyarrhythmia.

A shock channel may be configured with an endolymphatic electrode to produce a shocking vector that more directly passes through the left ventricle, which is the largest mass of the heart and is the region to which a defibrillation shock is most efficiently delivered. A shock delivered from an endolymphatic electrode may therefore exhibit a reduced DFT. Such a shocking vector may be produced, for example, by delivering a shocking voltage pulse to a thoracic duct electrode (as either anode or cathode) referenced to the implantable device housing, an atrial electrode, an SVC electrode, a left ventricular electrode, and/or a right ventricular electrode. The implantable device may be configured with an endolymphatic shock channel incorporating an electrode implanted in the thoracic duct, configured to monitor for the occurrence of a tachyarrhythmia via a cardiac sensing channel, configured to deliver a cardiac shock via the endolymphatic shock channel upon detection of a shockable tachyarrhythmia.

4. Exemplary Embodiments

In an exemplary embodiment, a cardiac rhythm management device incorporates an endolymphatic sensing, pacing, and/or shock channel configured with an electrode implanted in the thoracic duct. The endolymphatic sensing, pacing, and/or shock channel may also be configured with additional electrodes such as the device housing, an intra-cardiac electrode in an atrium or ventricle, a coronary sinus or cardiac vein electrode, an epicardial electrode, and/or a subcutaneous electrode. The device may then be programmed to record an endolymphatic electrogram generated from the endolymphatic sensing channel. Such a recorded endolymphatic electrogram may then be wirelessly transmitted to an external programmer, analyzed to detect cardiac ischemia, and/or analyzed to discriminate between a ventricular tachycardia and a supraventricular tachycardia. The device may also be programmed to deliver paces through an endolymphatic pacing channel in accordance with a programmed pacing mode and/or programmed to deliver shocks via an endolymphatic shock channel for terminating atrial or ventricular tachyarrhythmias.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for operating a cardiac rhythm management device, comprising:
    configuring an endolymphatic sensing channel with an electrode implanted in the thoracic duct; and,
    recording an endolymphatic electrogram generated from the endolymphatic sensing channel.

2. The method of claim 1 further comprising wirelessly transmitting the recorded endolymphatic electrogram to an external programmer.

3. The method of claim 1 further comprising analyzing the morphology of the recorded endolymphatic electrogram to detect cardiac ischemia.

4. The method of claim 1 further comprising analyzing the morphology of the recorded endolymphatic electrogram to discriminate between a ventricular tachycardia and a supraventricular tachycardia.

5. The method of claim 1 wherein the endolymphatic sensing channel is configured with the endolymphatically implanted electrode and a conductive implantable housing.

6. The method of claim 1 wherein the endolymphatic sensing channel is configured with the endolymphatically implanted electrode and an intra-cardiac electrode.

7. The method of claim 1 wherein the endolymphatic sensing channel is configured with the endolymphatically implanted electrode and a right ventricular electrode.

8. The method of claim 1 wherein the endolymphatic sensing channel is configured with the endolymphatically implanted electrode and a subcutaneously implanted electrode.

9. The method of claim 1 further comprising:
    configuring an endolymphatic shock channel with an electrode implanted in the thoracic duct; and,
    delivering a cardiac shock via the endolymphatic shock channel upon detection of a shockable tachyarrhythmia.

10. The method of claim 1 further comprising:
    configuring an endolymphatic pacing channel with an electrode implanted in the thoracic duct; and,
    delivering pacing pulses via the endolymphatic pacing channel in accordance with a programmed pacing mode.

* * * * *